United States Patent [19]

Dahne et al.

[11] Patent Number: 4,746,179
[45] Date of Patent: May 24, 1988

[54] WAVEGUIDE TO BE USED AS OPTICAL PROBE IN MULTIPLE INTERNAL REFLECTION SPECTROSCOPIC ANALYSIS

[75] Inventors: Claus Dahne, Onex; André Bregnard, Le Lignon; Georges Revillet, Onex; Ranald M. Sutherland, Carouge, all of Switzerland

[73] Assignee: Battelle Memorial Institute, Carouge, Switzerland

[21] Appl. No.: 880,548

[22] Filed: Jun. 30, 1986

[30] Foreign Application Priority Data

Jul. 1, 1985 [CH] Switzerland ............... 2799/85

[51] Int. Cl.$^4$ ............................................. G02B 6/00
[52] U.S. Cl. .............................. 350/96.10; 350/96.19; 356/133
[58] Field of Search ............... 350/96.10, 96.15, 96.19; 356/128, 133

[56] References Cited

U.S. PATENT DOCUMENTS 3,370,502  2/1968  Wilks, Jr. ..................... 356/133

OTHER PUBLICATIONS

Hansen et al, "Spectrometer Cells for Single ... Infrared Spectral Regions", North American Aviation Science Center, Canoga Park, Calif. *Analytical Chemistry*, vol. 36, No. 4, Apr. 1964, pp. 783–787.

*Primary Examiner*—John Lee
*Assistant Examiner*—Phan Heartney
*Attorney, Agent, or Firm*—Cushman, Darby & Cushman

[57] ABSTRACT

Waveguide apparatus for use in substance analysis has a waveguide, with a surface area in contact with the substance, for transmitting electromagnetic radiation along the axis of the waveguide whereby propagation characteristics of the radiation are altered in accordance with properties of the substance adjacent the waveguide. A waveguide entrance prism is positioned at the radiation entrance end of the waveguide, for guiding radiation into the waveguide. The prism has a first face arranged at an angle with the waveguide axis to cause radiation entering the prism to propagate along the waveguide. In one embodiment, a longitudinal partition is arranged adjacent the waveguide substantially parallel to the waveguide axis, for partitioning the waveguide surface area into at least two parts so that multi-substance analysis can be carried out. In another embodiment, the waveguide entrance prism includes a first face perpendicular to the waveguide axis, and second and third faces at an angle to both the waveguide axis and the first face. In effect, two entrance prisms are provided in the second embodiment. The second embodiment also includes a reflector and filter at the distal end of the waveguide to filter and reflect radiation back to the entrance prism.

19 Claims, 2 Drawing Sheets

WAVEGUIDE TO BE USED AS OPTICAL PROBE IN MULTIPLE INTERNAL REFLECTION SPECTROSCOPIC ANALYSIS

BACKGROUND OF THE INVENTION

The present invention concerns waveguides which transmit electromagnetic energy, e.g. visible, UV or IR radiation; such waveguides are usable as optical probes in devices for spectroscopically analyzing chemical or biochemical substances which, when it contact with the probe, modify some transmission parameters of this radiation in the waveguide. A measure of said parameters variation, for instance light absorption, diffraction, scattering, shift of the wavelength, fluorescence generation, etc. provides data directly related to the substance(s) to be analyzed. The latter may, either be dissolved in a liquid with which the waveguide is contacted, whereby the measurements will involve the bulk of the analyte, or it may react with a specific ligand applied to the guide surface, whereby a coating is formed whose rate of growth with time constitutes a distinctive feature of the substance to be analyzed.

Generally, such waveguides are laminar, flat or cylindrical fiber-like bodies and they assure the transmission of the light signal by multiple internal reflection at an angle of incidence $\theta$ larger than the critical angle $\theta_c$ (below which refraction occurs) but generally very close thereto.

An analytical device incorporating such kind of waveguides has been disclosed recently (see European Patent Application No. EP-A-84.810.601.9) as well as the measuring techniques pertaining to such apparatus. The waveguides disclosed in the present invention can be used in the said apparatus and constitute, indeed, particularly useful embodiments thereof. In the desciption that follows, direct reference to the said document will be made, the present waveguide being considered as directly usable as a component of the analytical apparatus disclosed and claimed therein.

The waveguide disclosed in the reference document comports a dual optical transmission element (51, 52; 71, 72; see FIGS. 1-3) whose geometry requires using, for injecting a light signal therein at an appropriate angle of incidence and to collect the signal exiting therefrom, optical means (mirrors) arranged in a relatively complicated relation. Indeed, because of the particular orientation of the input and output prisms of said optical elements (see FIGS. 1 to 3 of the reference document), the path of the light signals outside said elements is rather intricate and makes sharp angles with the direction of the waveguide. It was therefore desirable, for obvious constructive reasons, to provide a waveguide enabling the injection of an input signal in a direction generally parallel to its optical axis or at a substantially small angle to this direction, the output signal obeying roughly the same criteria.

Claim 1 discloses a waveguide in conformity with the above requirements. According to a preferred embodiment thereof, the angle ($\beta$) between the slant plane of the wedge bevelled volume and the parallel surfaces of the waveguide corresponds to 0.5 (90°−$\theta$).

Regarding the input and output signals, it should be noted that the output signal can in some cases derive directly from the input signal (or is a residue thereof) after this signal has been modified along the waveguide (for instance, partly absorbed) by the action of the medium in which the guide is placed; otherwise the output signal can consists of a radiation of a different kind (e.g. production of fluorescence) generated by the medium upon interaction with the evanescent wave component of the excitation signal. Such a fluorescence is then returned into the guide at the interface between the waveguide and the analyte and is transmitted therein at an angle of internal reflection which may or may not correspond to the angle $\theta$ of the excitation signal. If the difference is significant, the direction of the fluorescent ouput signal emerging from the guide may diverge from that of the input signal (this can for instance be of significance when the same prism is used as the input and the output) which situation may be constructively advantageous, it being possible to angularly offset the output detector relative to the position of the input source. Evidently, the output prism can be made so as not to coincide with the input prism and can be placed elsewhere on the guide relatively to the position of the input prism. For instance, the input prism can be at one end of the waveguide and the output prism can be at the other end. In this case the bevel angles of the two prisms can be alike or they can have different values, this being particularly the case if the excitation and response signal travel at different $\theta$ angles.

It is further remarked that, depending on the desired waveguide embodiments, the wedge-shaped portion of the guide can be singly bevelled or doubly bevelled. In other terms, in the case of a single bevel, only one of the main faces of the guide starts diverging from the other toward the end of the guide, the second of the main surfaces keeping parallel to the guide optical axis; in the other case, the second face also diverges in a manner symmetrical or unsymmetrical with the first one.

SUMMARY OF THE INVENTION

According to one embodiment of the waveguide of the invention, the structure is that of a rectangular parallelipipede of transparent material the end faces of which are perpendicular to the main surfaces (orthorombic prism). The bevelled end portion of this guide is formed from one or more triangular wedge-like prisms which include a 90° dihedral angle. The prisms are integral with the guide by one of their bevelled faces which lies against one the main parallel surfaces near the end thereof and they are oriented such that the free adjacent face of the dihedron extends in a direction parallel to the guide's end face or is a prolongation thereof, i.e. it extends normally to the optical axis of the guide (and to the main parallel surfaces thereof).

Thus, in the case where the guide comports, on the same main surface, an input prism and an output prism, and the exciting signal is applied to the prism normally to the input dihedral face (the wedge back) that prolongs the end face of the waveguide, i.e. it is directed in parallel relation with the main surfaces of the guide, the input light ray is transmitted therein (after internally hitting the bevelled plane) by multiple internal total reflection at the angle $\theta$ and it emerges, after its interaction with the analyte which is in contact with one or both of the main surfaces, by means of the output prism, still travelling according to the same direction.

According to one embodiment of the invention, a longitudinal partition is positioned adjacent the waveguide substantially parallel to the waveguide axis, for partitioning the waveguide surfaced area into at least two parts to allow multi-substance analysis. According to a second embodiment of the invention, the waveguide entrance prism includes two faces which cause the radiation to reflect into the waveguide. In effect, two prisms are located at the entrance portion of the waveguide. The second embodiment also includes a reflector and filter at the distal end of the waveguide to filter and reflect radiation back to the entrance prism.

BRIEF DESCRIPTION OF THE DRAWINGS

The annexed drawing allows to better understand the invention.

DETAILED DESCRIPTION OF THE PREFERRED EMBODIMENT

Figure 1:
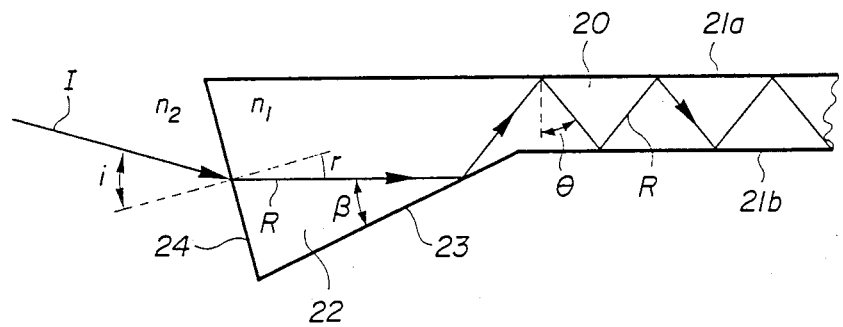
FIG. 1 is a schematic sectional view of a waveguide according to the invention.

The waveguide shown on FIG. 1 comprises a plate or slab 20 of transparent material, for instance glass, quartz or moulded plastics, crossed by a light signal I. Moulding can be achieved by injection or by compression. The main surfaces 21a and 21b of plate 20 are parallel and define the general direction of the optical axis of the guide. This waveguide comports at one end (the other end is not pictured on the drawing) a wedge-like portion 22, the bevel 23 of which is at an angle $\beta$ with surface 21b against which it lies flat. The back 24 of the wedge constitutes a facet end of the guide which is hit by the incident ray of the light signal at an angle i. The facet 24 is inclined relative to the main faces of the guide in a manner such (taking into account the values of the respective refractive indices of the guide (n1) and of the external medium (n2), for instance air) that if the ray I hits this facet 24 at an angle i, it is refracted into the guide at an angle r in a direction parallel to the optical axis of the guide. Under such conditions, the refracted signal R internally strikes the slant bevelled face 23 at an angle $\beta$ (having the aforementioned value) and it is reflected toward surface 21a which is reached at an angle $\theta$ ($\theta > \beta$) and wherefrom it is transmitted into the rectilinear portion of the guide by total internal reflection at this angle $\theta$.

The portion of the waveguide 20 not illustrated on the drawing (the end portion) can be symmetrically identical with the portion represented, or it can be different and correspond to the variants represented hereunder.

Figure 2:
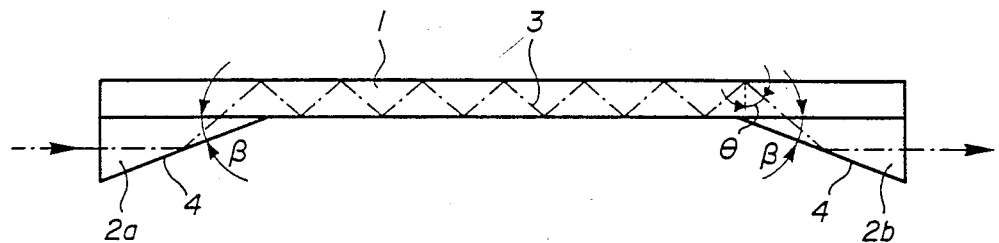
FIG. 2 is sectional view of a variant.

The waveguide shown on FIG. 2 is constituted by a plate or slab 1 of transparent material like in the case of the previous embodiment which comprises, applied against its lower surface and at the ends thereof, wedge-like prisms 2a and 2b acting as the input and output elements of a light ray 3, respectively; the refractive indices of the prisms are identical with the refractive index of the waveguide. The light signal travels inside of the guide by multiple total internal reflection at an angle $\theta$ (of incidence and reflection). The hypotenuse of each of prisms 2a and 2b makes an angle $\beta$ with the main faces of the waveguide, i.e. with the optical axis thereof; $\beta$ is defined above and also in claim 2.

Consequently, when the light signal 3 is injected normally to the dihedral face of the prism that prolongs the end-face of the guide (which is itself perpendicular to the guide axis), it is reflected at an angle $\beta$ by the hypotenuse of the prism and it will follow the path indicated by the arrow in the drawing. Since prism 2b is symmetrically oriented, the output signal will emerge from the guide in a direction which is still parallel with the waveguide axis.

The prisms 2a and 2b are bonded to the waveguide surface by means such that some discontinnuity which may exist between the joined elements does not interfere with the penetration of the light signal. Thus, the assembly can be achieved with a glue of refractive index as close as possible to that of the assembled elements. Preferably, the prisms are integral with the waveguide, i.e. the whole assembly is moulded integrally, for instance using injection-moulded plastics such as polymethacrylates, polystyrene, polycarbonates and the like.

In the drawing, the waveguide is pictured alone without the peripherals required for operation, for the sake of simplicity and clarity; it is understood that all such peripheral elements are classical and some are exemplified in the aforementioned reference application.

Figure 3:
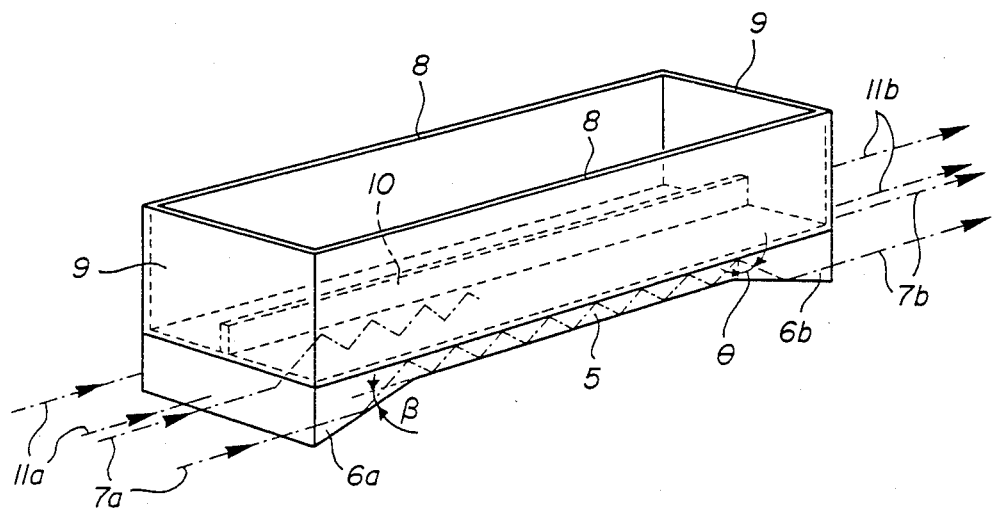
FIG. 3 is a perspective view of an analytical cuvette provided with a dual optical element which constitutes a variant embodiment of the guide represented on FIG. 2.

FIG. 3 represents an analytical cuvette-waveguide combination. The bottom 5 of the cuvette is constituted by a plane waveguide with parallel surfaces the end parts 6a, 6b of which are bevelled to provide wedge-shaped volumes integral with the bottom plate 5, the whole assembly being integrally moulded. The wedge-like ends are intended, as in the case of the embodiment of FIG. 2, to direct the wave energy represented by arrows 7a applied normally to the end-face of the dihedron so that it is reflected at an angle $\theta$ into the parallelipipede portion of the guide 5, whereby it is transmitted by total internal reflection. This wave energy is deflected into the prismatic volume 6b and emerges, as shown by arrows 7b, parallel-wise to the main planes of the guide 5.

The assembly represented further comprises, erected normally on the bottom 5, longitudinal and transversal walls 8 and 9, the whole assembly defining an analytical cuvette for containing an analytical solution which then will contact the upper surface of the waveguide 5. During analysis the wave energy 7a–7b transmitted by total reflection in the guide 5 is altered because of the interaction of the light with the analyte at the points of reflection. Such interactions can result, as described in documents EP-A-84.810.601.9 and 84.810.600.1, in some attenuation of the transmitted signal or in some other optical phenomena such as diffraction, fluorescence, etc. Whatever these variations, they will affect the signal 7b which emerges from the cell; this signal being detected, amplified and processed according to usual means to provide the desired analytical data.

The present cuvette is divided into two parallel compartments by a partition wall 10, each being suitable for effecting one independent analysis. A selection device (not represented but conventional, for instance a displaceable shutter plate or a double beam system) enables to inject the excitation light, either into the front compartment (wave-pack 7a–7b as represented on the drawing), or in the back compartment (wave-pack 11a–11b). For detecting the signals (7b, 11b), a single large detector can be used which measures both signals 7b and 11b in case of displaceable shutter plate. Otherwise, two independent detectors can also be used which collect the two signals independently and simultaneously. The means to process said signals into useful data and the means for display are known and illustrated in the reference application. Naturally, the present cell can have more than two compartments and can be designed to simultaneously achieve a corresponding number of analyses.

Figure 4:
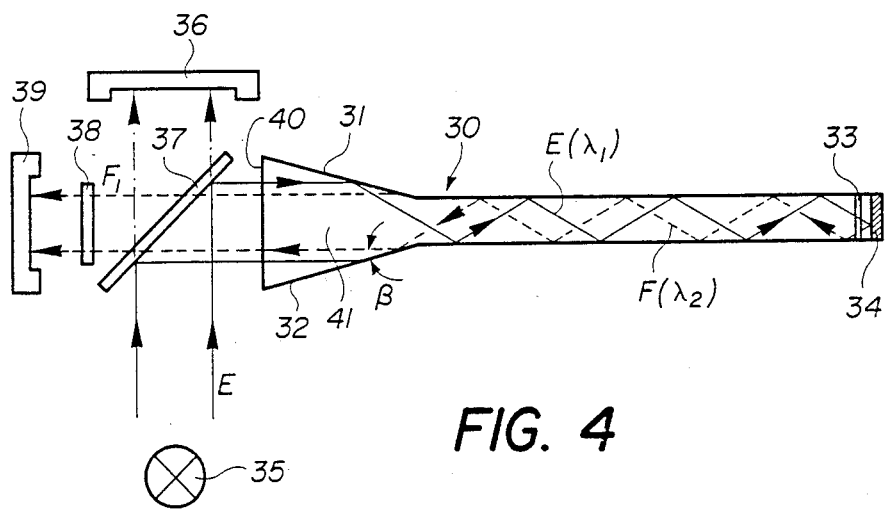
FIG. 4 is a schematic cross-sectional view of another modification including the peripheral elements involved for operation.

The modification represented on FIG. 4 comprises a waveguide 30 whose main surfaces are parallel together and an end 41 which is prismatic volume defined by faces 31 and 32 which both diverge by an angle β from the general direction of the main surfaces. The present waveguide comprises at the other end a filter 33 and a mirror 34. The drawing further shows schematically some of the peripheral organs required for operation, namely a source 35 for the excitation signal, a reference detector 36, a beam splitter 37, a filter 38 and a main detector 39.

The input signal E of wavelength $\lambda_1$ emitted by the source is injected, after being reflected by the beam splitter 37, into the waveguide perpendicularly to the back 40 of the wedge-like prism 41 and, by virtue of the slant walls 31 and 32, it is transmitted along the straight portion of the guide by internal reflection. Due to its interaction with an analytic solution in which the guide is immersed, the excitation signal E generates a fluorescence emission of wavelength $\lambda_2$. At the end of the waveguide, the $\lambda_1$ signal is stopped by the sharp cut-off filter 33 which, in contrast, transmits the fluorescence radiation F ($\lambda_2$). The latter is back reflected by the mirror 34 into the guide wherefrom it finally emerges and is collected by detector 39 after passing through the beam splitter 37 and the narrow-pass filter 38. It should be noted that, the mirror 34 and the filter 33 are not necessary for operation and can be omitted if desired, since the fluorescence generated at the solid/liquid interface by interaction between the excitation light evanescent component and the analyte is partly returned to the guide in the backward direction, whereby at least part of said fluorescence signal becomes available at the detector without the need of a reflective mirror. Alternatively, the waveguide 30 could be cylindrically shaped and comprise a frustoconical input/output portion.

The present invention is further exemplified by the following not limitative working cases: a cuvette of the type represented at FIG. 3 was used to perform an analysis of blood constituents, the measurements being directed to two distinctive factors, each of which being determined in one separate compartment of the cell. This analysis conforms with the measurements detailed in Example 5 to document EP-A-84.810.600.1 and refers to total hemoglobin analysis on one hand, and to glycosylated factors such as HbAlC on the other hand. For this test, the bottom of the front compartment of the cuvette is coated beforehand with an antibody specific to HbAlC whereas the other compartment remains untreated. An integral injection moulded cuvette made of plexiglas (including the wedge ends) was used, the refractive index ($n_1$) of which was 1.51; the refractive index ($n_2$) of the analyte (an aqueous solution) was 1.34; in this case, the calculated critical total reflexion angle $\theta_c$ is about 62.6°, as calculated from the known formula $\theta_c = \sin^{-1}(n_2/n_1)$. Consequently, the bevel angle β was selected at 12°, a value slightly below the approximate limit of 13.7°.

The dimensions of the cell were as follows: length 30 mm; width 10 mm; width of each compartment about 5 mm; content of each compartment 0.5–0.7 ml; Thickness of the waveguide 0.5 mm; height of the wedge 1.22 mm; length of the slant portion 5.6 mm.

The remaining operating elements corresponded to the data given in document EP-84.810.601.9 with the following modification: the beam from the source as well as the detector outside the cell are located on a straight line parallel to the cuvette bottom and passing through the back-facets of the wedges 6a, 6b. The operating conditions and the results were alike that disclosed in the aforementioned document.

In further experiments, the consequences resulting from deviations in the manufacture of injection moulded elements on the performance of a waveguide according to the invention were ascertained. The cuvette selected was similar to that of FIG. 3 and it was manufactured from extruded PMMA. The cell had a bottom (waveguide) 0.5 mm thick, a wedge angle of 12° and a wedge length of 5 mm. The test analyte was a 10 mg/ml hemoglobin solution. During the test the incident angle to the input prism was varied to approach as much as possible the limiting angular reflexion conditions. Indeed, although changing the incident angle from 90° to other values (using the right angle wedge) is outside the scope of the present invention (such a change will shift the refracted beam to a direction that is no longer parallel to the guide optical axis) it enables to easily determine whether the value selected for the bevel angle (in this case 12°) is correct or not within the range of dimensional tolerance inherent to industrial mouldings (deformations e.g. shrinkage, caused by temperature changes during the moulding process).

The following transmission values (arbitrary units) were found when varying the incident angle:

| Incident angle (°) | Transmission |
| --- | --- |
| 86 | 2463 |
| 87 | 2490 |
| 88 | 2784 |
| 89 | 2694 |
| 90 | 2511 |
| 91 | 2253 |
| 92 | 1874 |

The above results show that with a moulded bevel of 12°, the optimal incidence angle is 88° and not 90° as the case should normally be. Thus, for maximizing the performances within the scope of the invention, it is desirable to slightly increase the bevel angle within the available limits (i.e. between 12° and 13.85°, the upper limit controlled by the critical angle).

The bevel angle of the mould was therefore modified in the manufacture of new cells of identical design and was set arbitrarily to 14° and 16°. The results showed that better results were achieved with a moulding angle of about 14°; with 16°, the results were poor. This means that in view of the above mentioned manufacturing deviations, optimal results were obtained when the molding angle was set to a value slightly above what it should normally have.

We claim:

1. Waveguide apparatus for use in substance analysis, comprising:
   waveguide means having a surface area in contact with a substance, for transmitting electromagnetic radiation along an axis of said waveguide means whereby propagation characteristics of said radiation are altered in accordance with properties of said substance;

waveguide entrance prism means positioned at a radiation entrance end of said waveguide means, for guiding radiation into said waveguide means, said prism means including a first face arranged at an angle with said waveguide axis to cause said radiation entering said prism means to propagate along said waveguide means; and longitudinal partitioning means positioned adjacent said waveguide means substantially parallel to said waveguide axis, for partitioning said waveguide surface area into at least two parts.

2. Apparatus according to claim 1 wherein said prism means first face is at an angle $\beta$ with respect to said waveguide axis to cause said radiation to reflect from said first face into said waveguide means.

3. Apparatus according to claim 2 wherein said angle $\beta$ is positioned such that $\beta = 0.5(90° - \theta)$, where $\theta$ is ½ of the angle at which said radiation reflects along said waveguide means.

4. Apparatus according to claim 1 wherein said waveguide means and said waveguide entrance prism means are integrally formed.

5. Apparatus according to claim 1 wherein said waveguide means comprises a rectangular parallelipiped of transparent material having an entrance face, and wherein said waveguide entrance prism means comprises a triangular, wedge-shaped prism with a right dihedral angle, said prism having first and second facets adjacent a 90° angle, said first facet being substantially parallel to said waveguide axis, said second facet being substantially parallel to said parallelipiped entrance face.

6. Apparatus according to claim 1 further including waveguide exit prism means positioned at a radiation exit end of said waveguide means, for guiding radiation out of said waveguide means, said exit prism means including a first face arranged at an angle with said waveguide axis to cause said radiation exiting said prism means to propagate substantially parallel to said waveguide axis.

7. Apparatus according to claim 1 wherein said prism means comprises a material having a refractive index substantially the same as that of said waveguide means.

8. Apparatus according to claim 1 further including cuvette means for holding said substance in contact with said waveguide means surface area.

9. Apparatus according to claim 8 wherein said waveguide means comprises a bottom surface of said cuvette means.

10. Apparatus according to claim 1 further including:
reflecting means positioned adjacent an end of said waveguide means opposite said entrance end, for reflecting radiation propagating through said waveguide means back to said entrance end; and
filter means positioned between said reflecting means and said waveguide means end which is opposite said entrance end, for filting radiation propagating along said waveguide means.

11. Waveguide apparatus for use in substance analysis, comprising:
waveguide means having a surface area in contact with a substance, for transmitting electromagnetic radiation along an axis of said waveguide means whereby propagation characteristics of said radiation are altered in accordance with properties of said substance;
waveguide entrance prism means positioned at a radiation entrance end of said waveguide means, for guiding radiation into said waveguide means, said prism means including a first face substantially perpendicular to said waveguide axis, second and third faces both diverging from said waveguide means at an angle $\beta$ to said waveguide axis to cause said radiation entering said prism means to propagate along said waveguide means;
reflecting means positioned adjacent an end of said waveguide means opposite said entrance end, for reflecting radiation in said waveguide means back toward said entrance end; and
filtering means positioned between said reflecting means and said waveguide means and opposite said entrance end, for filtering radiation propagating along said waveguide means.

12. Apparatus according to claim 11 wherein said entrance prism means is formed as two triangular wedge-shaped prisms with a right dihedral angle, the hypotenuses of both said prisms diverging away from said waveguide means.

13. Apparatus according to claim 11 further including longitudinal partitioning means positioned adjacent said waveguide means substantially parallel to said waveguide axis, for partitioning said waveguide surface area into at least two parts.

14. Apparatus according to claim 11 wherein said angle $\beta = 0.5(90° - \theta)$, where $\theta$ is ½ of an angle at which said radiation reflects along said waveguide means.

15. Apparatus according to claim 11 wherein said waveguide means and said waveguide entrance prism means are integrally formed.

16. Apparatus according to claim 11 wherein said waveguide means comprises a rectangular parallelipiped of transparent material.

17. Apparatus according to claim 11 further including waveguide exit prism means positioned at a radiation exit end of said waveguide means, for guiding radiation out of said waveguide means, said exit prism means including a first face arranged at an angle with said waveguide axis to cause said radiation exiting said exit prism means to propagate substantially parallel to said waveguide axis.

18. Apparatus according to claim 11 further including cuvette means positioned adjacent said waveguide means, for holding said substance in contact with said surface area.

19. Apparatus according to claim 18 wherein said waveguide means comprises a bottom of said cuvette means.

* * * * *